US006825926B2

(12) United States Patent
Turner et al.

(10) Patent No.: US 6,825,926 B2
(45) Date of Patent: Nov. 30, 2004

(54) FLOW CELL FOR URINALYSIS DIAGNOSTIC SYSTEM AND METHOD OF MAKING SAME

(75) Inventors: Richard H. Turner, Mercer Island, WA (US); Dale A. Keiser, Wickenburg, AZ (US)

(73) Assignee: International Remote Imaging Systems, Inc., Chatsworth, CA (US)

( * ) Notice: Subject to any disclaimer, the term of this patent is extended or adjusted under 35 U.S.C. 154(b) by 0 days.

(21) Appl. No.: 10/696,898

(22) Filed: Oct. 29, 2003

(65) Prior Publication Data

US 2004/0095574 A1 May 20, 2004

Related U.S. Application Data

(60) Provisional application No. 60/427,872, filed on Nov. 19, 2002.

(51) Int. Cl.[7] ................................................ G01N 21/01
(52) U.S. Cl. .................... 356/244; 356/440; 250/461.1; 73/152.18
(58) Field of Search ................................. 356/244, 246, 356/440, 436, 73; 250/461.1; 73/152.18, 54.04

(56) References Cited

U.S. PATENT DOCUMENTS

| 4,338,024 | A | 7/1982 | Bolz et al. |
|---|---|---|---|
| 4,393,466 | A | 7/1983 | Deindoerfer et al. |
| 6,184,978 | B1 | 2/2001 | Kasdan et al. |
| 6,473,172 | B1 | 10/2002 | Pelmulder |
| 6,608,680 | B2 * | 8/2003 | Basiji et al. ................ 356/338 |
| 6,755,079 | B1 * | 6/2004 | Proett et al. ............. 73/152.18 |

* cited by examiner

Primary Examiner—Gregory J. Toatley, Jr.
Assistant Examiner—Sang H. Nguyen
(74) Attorney, Agent, or Firm—Gray Cary Ware & Freidenrich LLP (57) ABSTRACT

A flow cell for examining specimen fluid flowing within sheath fluid. A housing defines a hollow fluid passage that includes a geometric focusing portion in which the fluid passage narrows in height and an examination area. A cannula injects specimen fluid into the fluid passage as a stream of the specimen fluid with an initial velocity. The sheath fluid flows through the fluid passage, having a first velocity as it passes the point the specimen fluid is injected. The initial velocity is less than the first velocity, which focuses down the height of the specimen fluid stream via linear flow rate focusing. The narrowing geometric focusing portion of the fluid passage also focuses down the height of the specimen fluid stream via geometric focusing. A microscope and camera capture images of the focused down specimen fluid stream passing through the examination area.

25 Claims, 8 Drawing Sheets

FLOW CELL FOR URINALYSIS DIAGNOSTIC SYSTEM AND METHOD OF MAKING SAME

This application claims the benefit of U.S. Provisional Application No. 60/427,872, filed Nov. 19, 2002, which is incorporated herein by reference.

FIELD OF THE INVENTION

The present invention relates to methods and systems for analyzing particles in a dilute fluid sample, and more particularly to a flow cell for producing a thin stream of specimen fluid from which optical images thereof can be obtained.

BACKGROUND OF THE INVENTION

Methods and systems for analyzing particles and particularly sediments are well known in the art, as disclosed in U.S. Pat. Nos. 4,338,024 and 4,393,466, which are incorporated herein by reference. Such systems utilize a flow cell though which fluid samples (specimen fluids) are passed, and a particle analyzer for capturing still frame images of the fluid passing through the flow cell. Thus, the flow cell positions and presents the sample fluid containing particles of interest for analysis. The more accurately that the sample fluid is positioned by the flow cell, the better the analysis of the particles therein that can be made.

Typical flow cells cause the sample fluid, and a sheath fluid that buffers the sample fluid, to flow together from a large entry chamber into a small cross section examination area or region. The transition from the inlet or entry chambers to the examination region forms a hydrodynamic lens that squeezes both the sample fluid and the sheath fluid proportionally into the smaller space. Where the particles of interest are microscopic particles, the resulting cross-section space occupied by the sample fluid must be positioned within the depth of field of the analyzer, such as an optical system or a laser system, to obtain the best analytical information. For the best hydrodynamic focus, a large area of sheath flow must envelop the small area of sample fluid without any swirling or vortices. Thus, uniform flow of sample and sheath fluids through the flow cell is essential for optimal operation of particle analyzers. The sample mass transfer characteristics should be reproducibly controlled, so that the specimen cross section is sufficiently wide (e.g. 1 mm wide) for the specific application and measurement technique, with a thickness commensurate with the requirements of the detection method, while the fluid velocity is slow enough to permit stopped flow analysis, but fast enough to preclude particle overlap.

Traditionally, the flow of specimen and sheath fluids has been controlled by using air pressure to drive these fluids to and through the flow cell. The air pressure applied to each fluid can be adjusted to change the relative flow rate of that fluid through the flow cell. However, such adjustments must be made empirically to obtain the best image capture results, since many other factors affect the flow rate of each fluid as well (e.g. fluid viscosity, flow path resistance, etc.) which can vary system to system, and from fluid to fluid. Moreover, it has been found that flow cell performance can be highly sensitive to the position (translational and angular) of the needle or cannula used to inject the specimen fluid into the flow cell. Thus, it can be a time consuming task to manufacture, test and/or operate the flow cell with optimal and reliable performance.

SUMMARY OF THE INVENTION

The present invention is a flow cell for examining specimen fluid flowing with sheath fluid. The flow cell includes a housing defining a hollow fluid passage that has an injection point, a geometric focusing portion in which the fluid passage narrows in a cross section dimension thereof, and an examination area, a cannula having an output end disposed at the injection point in the fluid passage, a first direct flow control pump for pumping the sheath fluid through the fluid passage such that the sheath fluid has a first known velocity at the injection point, a second direct flow control pump for pumping the specimen fluid through the cannula such that the specimen fluid is injected into the fluid passage by the cannula output end as a stream of the specimen fluid having a second known velocity at the injection point wherein the second known velocity is different from the first known velocity, and a measurement device for measuring a parameter of the specimen fluid stream passing through the examination area. A cross section dimension of the specimen fluid stream is focused by the sheath fluid via linear flow rate focusing and by the narrowing geometric focusing portion of the fluid passage via geometric focusing.

Another aspect of the present invention is a method of flowing specimen fluid and sheath fluid through a hollow fluid passage of a flow cell having an injection point, a geometric focusing portion in which the fluid passage narrows in a cross section dimension thereof, and an examination area. The method includes flowing the sheath fluid through the fluid passage such that the sheath fluid has a first known velocity at the injection point, injecting the specimen fluid into the fluid passage at the injection point as a stream of the specimen fluid having a second known velocity wherein the second known velocity is different from the first known velocity, and measuring a parameter of the specimen fluid stream passing through the examination area. A cross section dimension of the specimen fluid stream is focused by the sheath fluid via linear flow rate focusing and by the narrowing geometric focusing portion of the fluid passage via geometric focusing.

One more aspect of the present invention is a method of forming a cannula from a hollow tube having first and second ends and a first cross-section shape. The method includes cutting a hollow tube to a desired shape wherein the cut tube has a first end and a second end and a first cross-section shape, inserting a first mandrel having a first thickness into the first end, crushing the first end onto the first mandrel, removing the first mandrel from the first end, and then inserting a second mandrel having a second thickness into the first end wherein the second thickness is less than the first thickness, crushing the first end onto the second mandrel, and removing the second mandrel from the first end. After the crushings of the first end, the first end has a second cross-section shape that is different from the first cross-section shape.

Other objects and features of the present invention will become apparent by a review of the specification, claims and appended figures.

DETAILED DESCRIPTION OF THE PREFERRED EMBODIMENTS

The present invention is a flow cell that achieves improved performance by combining geometric focusing and linear flow rate focusing to achieve a desired specimen layer thickness at the examination area, where the specimen velocity is small enough to ensure that a strobed image system can capture a clear still-image of the flowing specimen, and is great enough to ensure the captured images do not overlap each other. The relative velocities of the specimen and sheath fluids are carefully controlled using direct flow control pumps.

Figure 1A:
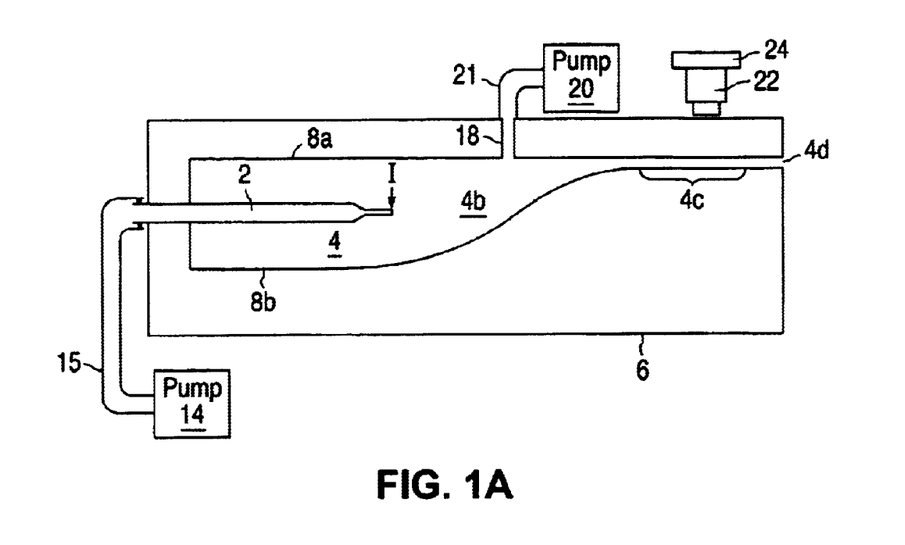
FIG. 1A is a side cross-section view of the flow cell of the present invention.
Figure 1B:
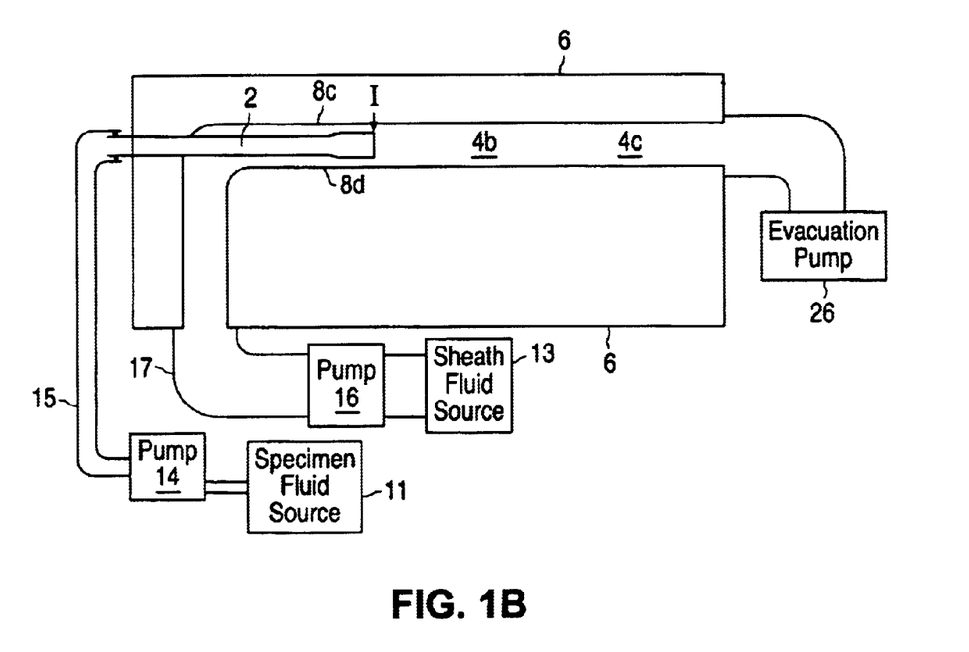
FIG. 1B is a top cross-section view of the flow cell of the present invention.

The flow cell 1 of the present invention is illustrated in FIGS. 1A and 1B, and includes a cannula 2 for injecting specimen fluid into a fluid passage 4 defined by a flow cell housing 6. The fluid passage 4 includes an inlet 4a for receiving sheath fluid, a geometric focusing portion 4b where a cross section dimension (e.g. height) of the passage decreases, a examination area 4c in which images of the specimen fluid are captured, and an outlet 4d where the specimen and sheath fluids exit the flow cell 1. Housing 6 is made of a rigid material (e.g. plastic) that defines top, bottom, left side and right side walls (8a, 8b, 8c and 8d respectively) of passage 4 for guiding fluid therethrough. A microscope 22 and camera 24 (which are well known in the art and thus not described herein in any further detail) together form an imager that captures still frame images of the specimen fluid passing through the examination area 4c of passage 4.

As shown in FIGS. 1A and 1B, the flow rate of specimen fluid into cannula input end 2a, through cannula 2, and out cannula output end 2b is controlled by a pump device 14, which supplies the specimen fluid 10 from a specimen source 11 (e.g. container, test tube) via a supply tube 15. The flow rate of sheath fluid 12 from a sheath fluid source 13 (e.g. container), into passage inlet 4a, through passage 4, and out passage outlet 4d is controlled by a pump device 16, which supplies sheath fluid via supply tube 17. An optional port 18 can be formed along top wall 8a of passage 4, and connected to a vacuum pump 20 via vacuum tube 21 (as shown in FIG. 1A), which can be used to remove air bubbles from passage 4.

Cannula 2 (also shown in FIG. 2) includes an input end 2a (for receiving specimen fluid), and an output end 2b (for injecting specimen fluid into passage 4 as a fluid stream). Input end 2a preferably has a round cross-section, which preferably tapers down to an elliptical-like cross-section at the output end 2b. As a non-limiting example, the cannula output end 2b can have a width (W) of about 2 mm (i.e. wider than the width of the viewing area for the microscopic objective) and a height (H) of between about 50 microns and about 400 microns (preferably between about 150 to 300 microns). Because the elliptical output end 2b is tapered down from the cannula input end 2a (i.e. has a smaller cross-section area), the linear flow rate of specimen fluid traveling through input end 2a is smaller than that traveling through output end 2b.

Figure 3:
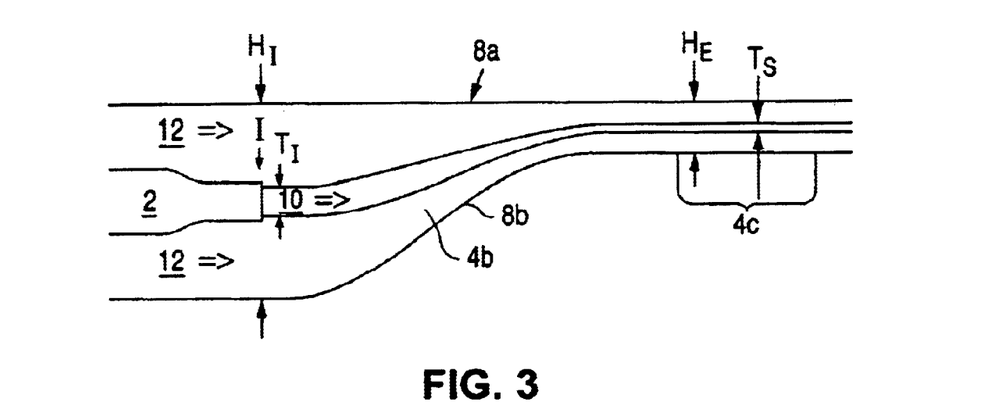
FIG. 3 is a side cross-section view of the flow cell of the present invention, illustrating the geometric focusing of the specimen fluid exiting the cannula.

The present invention utilizes both geometric and linear flow rate focusing. FIG. 3 illustrates geometric focusing, where specimen fluid 10 is injected into sheath fluid 12 flowing through passage 4 at an injection point I (i.e. the output end 2a of cannula 2 defines the injection point I within passage 4). Geometric focusing is caused by the narrowing of the passage 4. In the example shown in FIG. 3, the fluid passage 4 has a rectangular cross sectional shape, where bottom wall 8b slopes up toward upper wall 8A (which is planar), thus reducing the height (and thus the cross sectional area) of passage 4. Geometric focusing causes a reduction in stream thickness between the point of the specimen injection I and the point of specimen examination (area 4c). The specimen fluid stream thickness $T_S$ (e.g. height) at the examination area 4c of passage 4, as a result of geometric focusing alone (assuming equal linear flow rate of specimen and sheath fluids at the injection point I, and a rectangular cross sectional area that is being reduced in one dimension only), can be calculated as:

$$T_S = \frac{T_I \cdot A_E}{A_I} \quad (1)$$

where $T_I$ is the thickness (e.g. height) of the specimen stream at the injection point I, $A_I$ is the cross section area of the flow cell passage 4 at the injection point I, and $A_E$ is the cross section area of the examination area 4c of passage 4. If left and right side walls 8c and 8d are planar (so the passage has a uniform width in that dimension), then the specimen fluid stream thickness $T_S$ is:

$$T_S = \frac{T_I \cdot H_E}{H_I} \quad (2)$$

where $H_I$ is the height of passage 4 at the injection point I, and $H_E$ is the height of the examination area 4c of passage 4. It should be noted that if both the width and height are changed (i.e. changes in two orthogonal cross section dimensions), and/or a non-rectangular passage is used (i.e. cylindrical, oval, etc.) where one or more cross section dimensions are changed, then the calculation of the specimen fluid stream dimensions becomes more complicated, but focusing can occur in more than one dimension concurrently.

Figure 4:
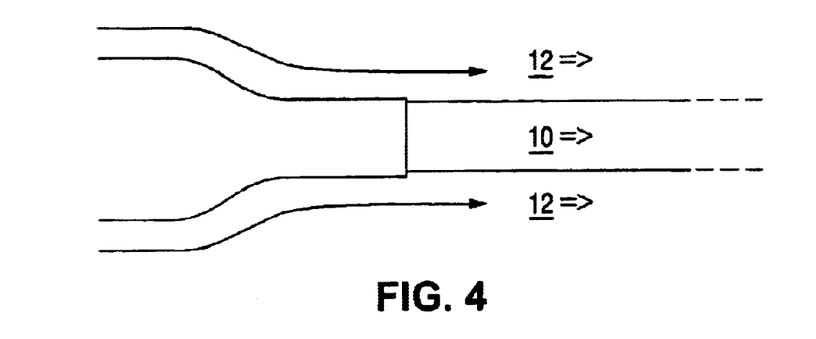
FIG. 4 is a side view of specimen fluid exiting the cannula without linear flow rate focusing.
Figure 5:
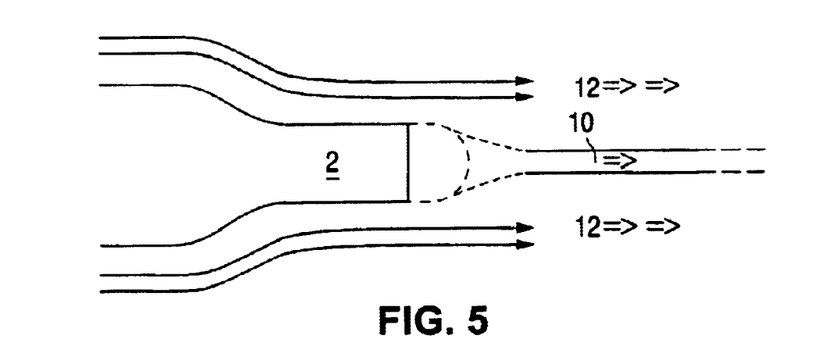
FIG. 5 is a side view of specimen fluid exiting the cannula with linear flow rate focusing.
Figure 6:
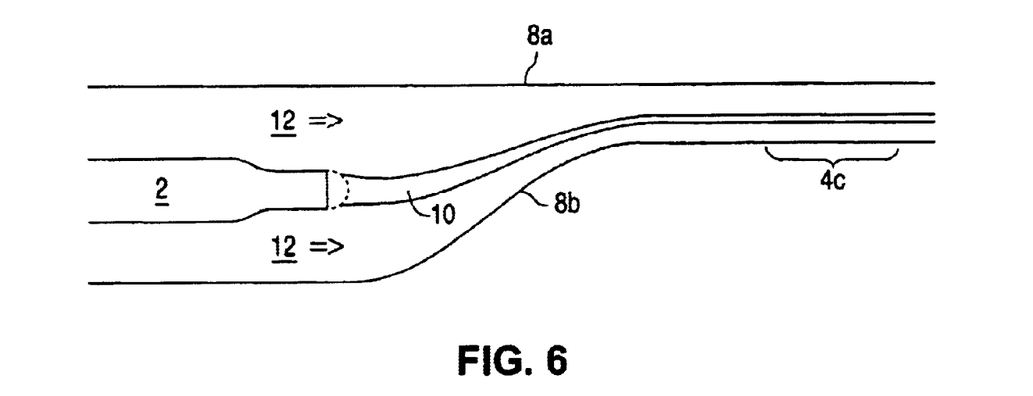
FIG. 6 is a side cross-section view of the flow cell of the present invention, illustrating geometric and linear flow rate focusing of the specimen fluid exiting the cannula.

Linear flow rate focusing of the specimen fluid occurs when the velocity of the specimen fluid differs from that of the sheath fluid. In particular, if the velocity of the sheath fluid passing the output 2b of cannula 2 is matched to the velocity of the specimen fluid exiting the cannula 2, the specimen fluid maps into the volume of the sheath fluid with the same shape as the output end 2b of cannula 2 (see FIG. 4). In that case, there is no linear flow rate focusing (i.e. there is a focusing ratio of one-to-one), and a non-focusing ratio R of sheath fluid mass to specimen fluid mass flowing past injection point I is created (which for similar liquids is the same as the ratio of cross section areas of the two liquids). However, pumps 14 and 16 supply specimen and sheath fluids at known and different velocity rates so that the initial specimen fluid velocity at the point of injection I is less than the sheath fluid velocity at that same point. Thus, a focusing ratio R of fluid masses is created where the thickness (e.g. height) of the specimen fluid is reduced just beyond the injection point I via linear flow rate focusing, as shown in FIG. 5. The (faster) flowing sheath fluid speeds up the (slower) moving specimen fluid stream, thinning the specimen fluid stream. Later downstream the specimen and sheath fluid velocities will eventually match, at which point no additional linear flow rate focusing occurs, but the height of the specimen stream has already been focused down by linear flow rate focusing. FIG. 6 illustrates the combination of geometric focusing and linear flow rate focusing.

In designing and operating the flow cell, the optical characteristics (e.g. optical focus, strobe and capture speeds, etc.) of the imager (i.e. microscope 22 and camera 24) will dictate the desired or optimal specimen fluid flow thickness and velocity through the examination area. The imager will also probably dictate the desired cross section area of the examination area of the flow cell. From there, the remaining flow cell dimensions, the cannula dimensions, and the initial sheath/specimen fluid velocities must be determined so that the resulting flow cell produces the desired examination conditions in the examination area 4c. Many of the design and operating parameters of the flow cell can be calculated, starting with the fact that the mass transfer rate (velocity times cross section area) of the fluids at any cross-section perpendicular to the flow direction is the same (i.e. conservation of fluid mass transfer because there is no fluid compression). Since the ratio of sheath fluid to specimen fluid is typically very high (e.g. 25:1), the cross section of the specimen fluid can be ignored when calculating mass transfer of the sheath fluid, which is focused purely by geometric focusing. A very good approximation of the relationship between sheath fluid velocities and cross sections can be obtained by assuming (for calculation purposes) that the sheath fluid alone completely fills both the insertion point and examination area portions of passage 4. With this assumption, the mass transfer equation gives the following relationship:

$$V_I \cdot A_I = V_E \cdot A_E \quad (3)$$

where $V_I$ and $V_E$ are the sheath fluid velocities at the passage's injection point I and examination area 4c, respectively, and $A_I$ and $A_E$ are the passage's cross section areas at the passage's injection point I and examination area 4c, respectively.

The mass transfer equation also gives the following relationship for the sample fluid:

$$V_{SI} \cdot A_{SI} = V_{SE} \cdot A_{SE} \quad (4)$$

where $V_{SI}$ and $V_{SE}$ are the sheath fluid velocities at the passage's injection point I and examination area 4c, respectively, and $A_{SI}$ and $A_{SE}$ are the cross section areas of the specimen fluid flow at the injection point I and examination area 4c, respectively.

Figure 2:
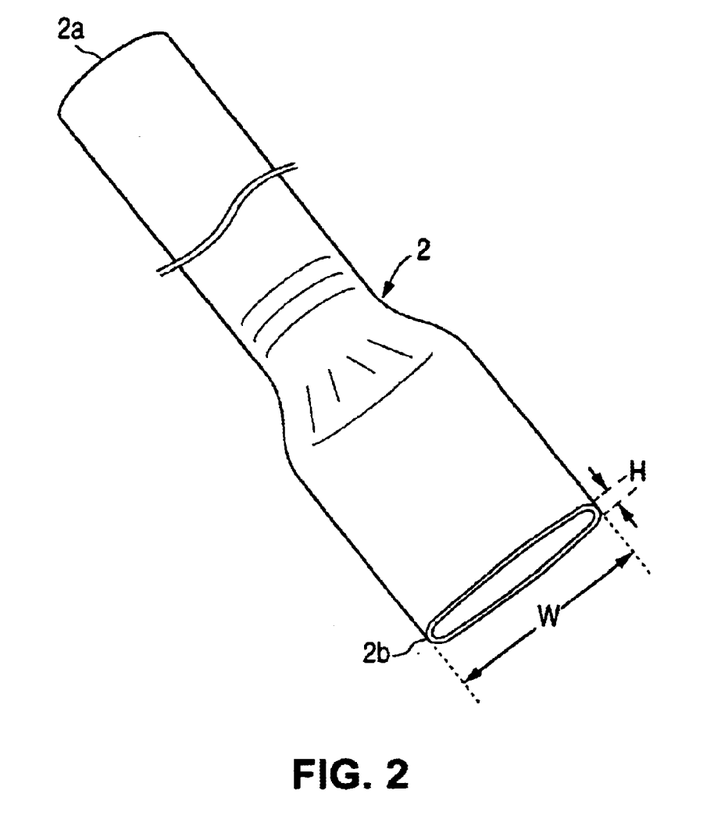
FIG. 2 is a perspective view of the cannula of the present invention.

As stated above, the optical characteristics of the imager will dictate the desired specimen fluid velocity $V_{SE}$ and cross section area $A_{SE}$ values at the examination area, as well as the examination area cross section $A_E$. Since the sheath and specimen fluid velocities $V_E$ and $V_{SE}$ in the examination area are equal to each other, then from equations 3 and 4:

$$\frac{V_I \cdot A_I}{A_E} = \frac{V_{SI} \cdot A_{SI}}{A_{SE}} \quad (5)$$

where the specimen fluid cross section area $A_{SI}$ at the injection point will be equal to the cross section area of the output end 2b of cannula 2, and the cross section areas $A_E$ and $A_{SE}$ are known from the imager's optical requirements. From these relationships, the cross section area of the passage at the injection point $A_I$, and the specimen/sheath velocities $V_{SI}$ and $V_I$ can then be calculated to produce the desired examination conditions. It has been determined that actual flow cells, which have been reduced to practice using the above formulas, perform as predicted by the above described equations.

The above equations point out the importance of knowing what the specimen/sheath velocities $V_{SI}$ and $V_I$ are, and the need to control those velocities with sufficient precision to produce the desired flow conditions in the flow cell, and to do so even though the viscosity of these fluids can routinely change. The prior art method of utilizing air pressure is insufficient, as this technique does not reliably produce known fluid velocities, especially with changing viscosities and back pressures. Therefore, the present invention preferably utilizes a direct flow control pump, which is a pump that produces a constant and known flow rate despite vast changes in fluid viscosity and back pressure.

One example of a direct flow control pump is a displacement (e.g. tubing or peristaltic) pump for pumping the sheath and specimen fluids through the flow cell. Displacement pumps are known in the art, and include one or more rollers that roll along flexible tubing that contains the liquid to be pumped. The roller creates a moving occlusion in the compression tube that pushes the fluid along the length of the tubing, drawing fluid into an input end of the tubing and forcing fluid out an output end of the tubing. Displacement pumps are advantageous because the velocity of the roller along the tubing equals the velocity of the fluid in the tubing. Since the cross section area of the tubing is known, a direct correlation between the roller velocity and the velocity of the pumped fluid at the injection point (through a known geometry) can be established, because fluid velocity and back pressure won't affect the speed of the roller. For example, since mass transfer between each pump and the flow cell is preserved, the mass transfer equation gives the following relationships:

$$V_{P1} \cdot A_{P1} = V_I \cdot A_I \quad (6)$$

$$V_{P2} \cdot A_{P2} = V_{SI} \cdot A_{SI} \quad (7)$$

where $V_{P1}$ and $A_{P1}$ are the roller velocity and tubing cross section area for the sheath fluid displacement pump 16, and $V_{P2}$ and $A_{P2}$ are the roller velocity and tubing cross section area for specimen displacement pump 14. Since the cross section areas for these equations are known and fixed, pump roller velocities can be directly correlated to the specimen/sheath fluid velocities at the injection point of the flow cell, thus allowing the system to reliably create and monitor the desired known fluid flows inside the flow cell simply by moving the pump rollers at controlled and known speeds.

Figure 7A:
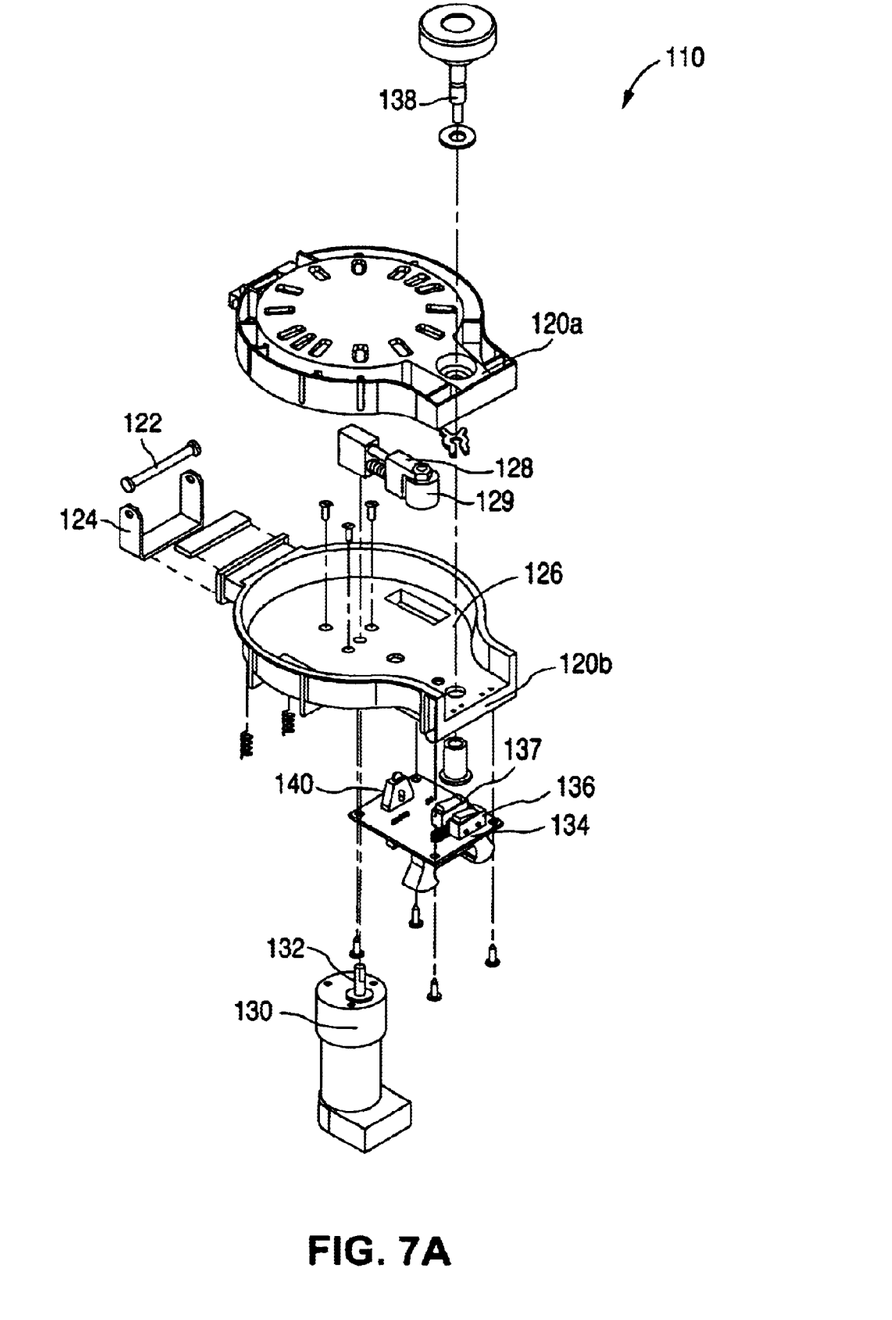
FIG. 7A is an exploded view of a displacement pump assembly.
Figure 7B:
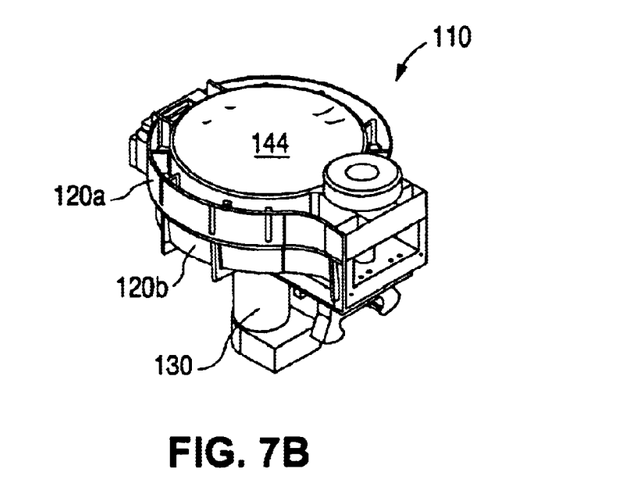
FIG. 7B is a perspective view of the displacement pump assembly.

An exemplary displacement pump for use with the flow cell of the present invention is illustrated in FIGS. 7A-7B. The pump 110 includes a housing 120 having upper and lower housing portions 120a/120b respectively, that are hingedly attached to each other by a hinge 122 and hinge bracket 124. When upper housing 120a is closed over lower housing 120b, an annular cavity 126 is defined thereby. A roller arm 128, which is preferably spring loaded, is disposed in the cavity 126. Roller arm 128 has a proximal end at the center of the cavity 126, and a distal end with an outwardly facing compression roller 129 mounted thereon. A motor 130 has a drive shaft 132 that extends into the cavity 126 and is attached to the proximal end of the roller arm 128, for rotating the roller 129 around the periphery of the cavity 126. A sensor assembly 134 is mounted to the lower housing 120b and includes a sensor switch 136 for detecting a closure pin 138 from the upper housing 120a, indicating that the upper housing 120a is in a closed position over lower housing 120b. Sensor assembly 134 also includes a sensor switch 137 that detects the presence of the cassette assembly 112 in cavity 126, and a sensor 140 that detects and verifies the position of the roller arm 128.

Figure 8A:
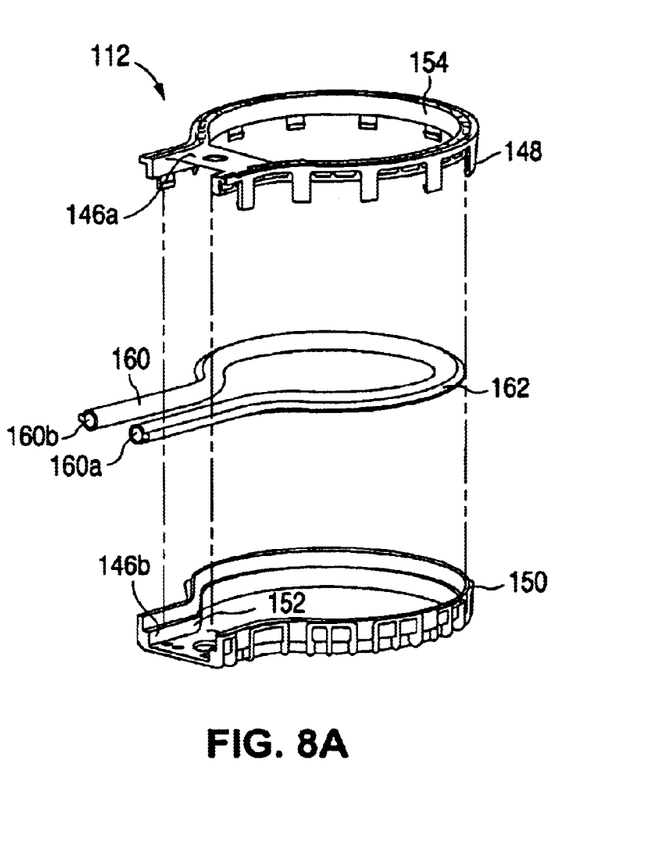
FIG. 8A is an exploded view of the cassette assembly for the displacement pump.
Figure 8B:
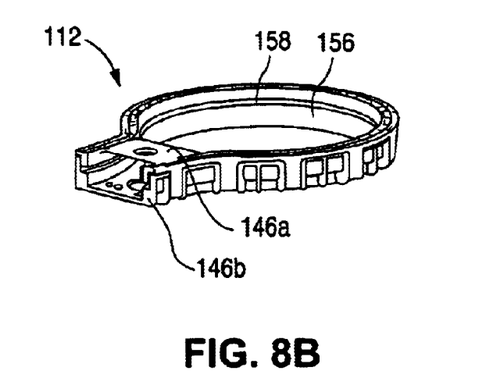
FIG. 8B is a perspective view of the cassette assembly (without the compression tube) of the displacement pump.
Figure 8C:
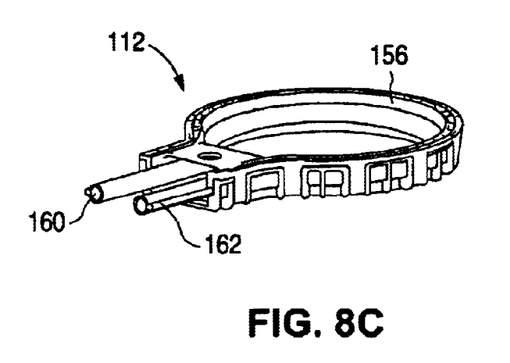
FIG. 8C is a perspective view of the cassette assembly of the displacement pump.

FIGS. 8A-8C illustrate the cassette assembly 112, which includes a housing 146 having upper and lower cassette housing portions 146a/146b respectively, that snap together via engagement tabs 148 that extend from the upper cassette housing 146a and engage with lower cassette housing 146b. Lower cassette housing 146b includes an annular sidewall 150 with a shoulder 152 extending from an inner surface of the sidewall 150. Upper cassette housing 146a includes an annular sidewall 154. When upper/lower cassette housings 146a/146b are snapped together, upper cassette sidewall 154 fits inside lower cassette sidewall 150, where sidewall 154 and the shoulder portion of sidewall 150 together define an inwardly facing annular compression surface 156. Upper cassette sidewall 154 is positioned a fixed distance away from shoulder 152 to define a channel 158 in the annular compression surface 156.

A hollow compression tube 160 is removably disposed along the compression surface 156. The compression tube 160 includes a flange 162 adhered thereto or integrally formed therewith. The flange 162 snuggly inserts into channel 158 with a friction fit that evenly secures compression tube 160 against compression surface 156. Preferably, flange 162 is a solid tube-shaped member that is integrally formed as part of the compression tube 160, and that has a thickness corresponding to the width of channel 158. The compression tube 160 has an input end 160a and an output end 160b.

To assemble pump 10, upper and lower cassette housings 146a/146b are snapped together, with a compression tube 160 secured against compression surface 156 via flange 162 (held in channel 158). The upper pump housing 120a is rotated open (away from lower pump housing 120b), and the cassette assembly 114 is inserted in lower pump housing 120b. The upper pump housing 120a is then closed, securely holding cassette assembly 112 in cavity 126.

When motor 130 is activated, roller arm 128 rotates within the cavity 126, so that roller 129 engages with compression tube 160 and compresses it against compression surface 156. The spring loaded roller arm 128 ensures that roller 129 is compressed against compression tube 160 with the desired amount of force, so that roller 129 creates an occlusion in the compression tube 160 which moves along the length of tube 160 as roller arm 128 makes a single revolution within cavity 126. The moving tube occlusion pushes a known quantity of fluid through the compression tube 160 in a uniform manner. By the time the roller arm 128 completes its single revolution, the roller 129 has moved along the entire length of the compression tube portion that is disposed on compression surface 156, and has disengaged from compression tube 160. The pump shown in the figures occludes the compression tube during (or for) 285 degrees of the rotation of roller arm 128, leaving 75 degrees of rotation where the roller 129 does not compress tube 160.

Ideally, the diameter of the compression tube 160 is selected so that the desired amount of fluid for a single process step (e.g. collection of images via a flow cell) can be produced by a single revolution of the roller arm 128, thus avoiding any pulsations caused by the repeated engagement and disengagement of the roller 129 with compression tube 160. By continuously anchoring the compression tube 160 against the compression surface (i.e. using the continuous flange 162 engaged in the continuous channel 158), tube squirm and fluid flow variations caused therefrom are avoided. A uniform delivery of fluid volume results from each incremental degree of rotation of roller arm 128. When the pump is inactive, the roller 129 is preferably parked in a default or rest position shown in FIG. 7A, where the roller 129 does not contact the compression tube 160, thus preventing premature tube failure due to the formation of flat spots therein. However, roller 129 can be temporarily parked on compression tube 60 so that the (stalled) tube occlusion acts as a temporary pinch-valve for the fluid inside compression tube 60.

The removable cassette 112 allows for easy replacement of the compression tubing 160 by the user. Insertion of the flange 162 into channel 158 is convenient and provides a repeatable positioning of the tubing 160 against compression surface 56. The tubing 160, and/or the cassette assembly 112 in its entirety, can be replaced by the user as tube 160 ages, ideally without the use of any tools. Closing upper housing 120a onto lower housing 120b compresses the cassette assembly 112 to secure compression tubing 160 and compression surface 156 in place (relative to pump assembly 110 and in particular roller 129). The clamping features of both the cassette assembly 112 and pump assembly 110 provide repeatable and convenient assembly and performance of the pump. The pump preferably uses tubing 160 having a symmetrical cross-section, which permits more uniform fabrication of the tubing and more repeatable pump performance, and is ideal for clamping features of the cassette assembly 112.

Figure 9:
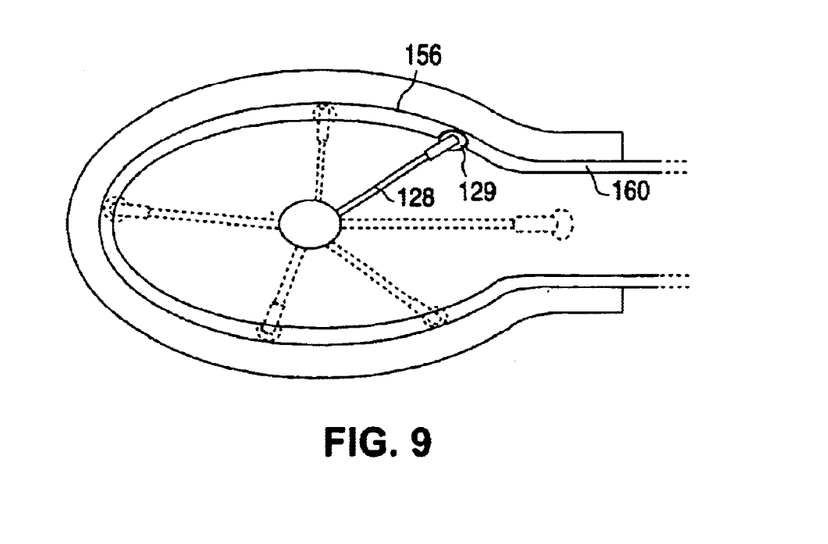
FIG. 9 is a top view of an alternate embodiment of the displacement pump.
Figure 10:
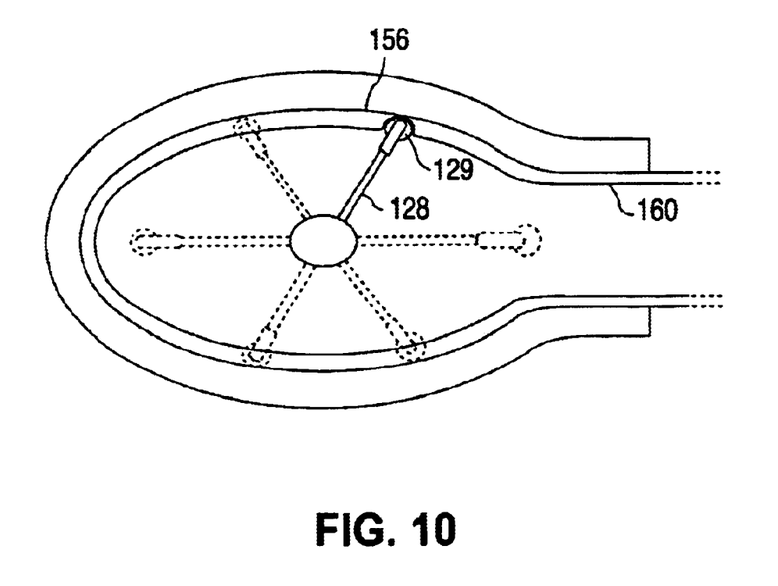
FIG. 10 is a top view of a second alternate embodiment of the displacement pump.
Figure 11:
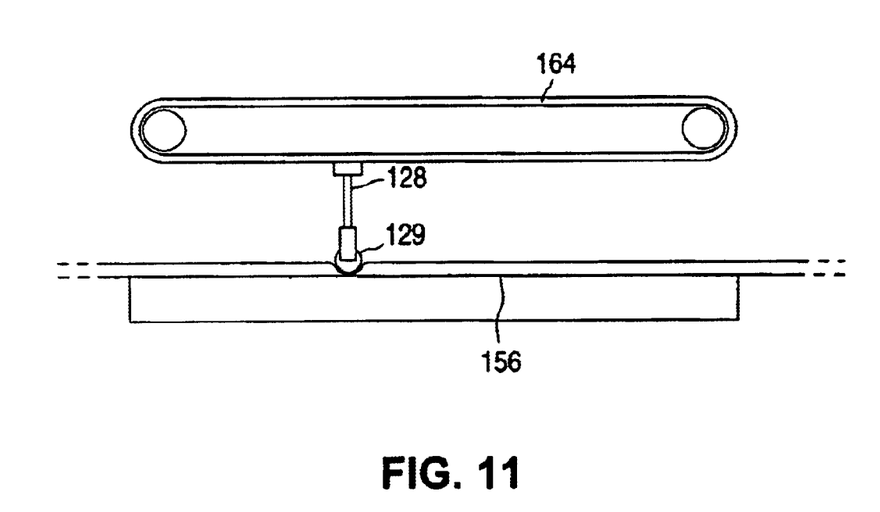
FIG. 11 is a side view of a third alternate embodiment of the displacement pump.

It should be noted that while pump housing portions 120a/120b are shown hingedly attached, they could instead snap together in the manner shown for cassette housing portions 146a/146b, and vice versa. Arm 128 need not necessarily be spring loaded. Compression surface 156 need not be circular, so long as the spring loaded roller arm 128 can maintain a desired minimal force for compressing compression tube 160. For example, the compression surface could be elliptical, where the rotating spring loaded roller arm has enough longitudinal travel (along the length of arm 128) to maintain contact with the compression tube 160 with sufficient force during the arm's revolution, as illustrated in FIG. 9. Alternately, the amount of longitudinal travel of the rotating arm could be more limited, where the roller 129 ceases compression of, and even possibly loses contact with, the compression tube at multiple points through its revolution, as illustrated in FIG. 10. In this case, the roller 129 twice loses contact with the compression tube 160, so that the pump produces two separate pulses of fluid flow per full revolution of the arm 128. In fact, roller 129 need not rotate about a fixed point, but can include translational movement, as shown in FIG. 11. In this embodiment, spring loaded arm 128 is connected to a moving conveyor belt or track 164 that moves roller 129 along a planar compression surface 156. One or more additional roller arms 128 (with rollers 129) can be added to belt/track 164, so long as only one roller is engaged with compression tube 160 at any given time.

It should be noted that an evacuation pump 26 can be used to withdraw the sheath and specimen fluids from the passage outlet 4d. Alternately, sheath pump 16 could be omitted from the flow cell system, and evacuation pump 26 can be a displacement pump that acts to draw the sheath fluid through the flow cell at known and controlled velocities.

Figure 12:
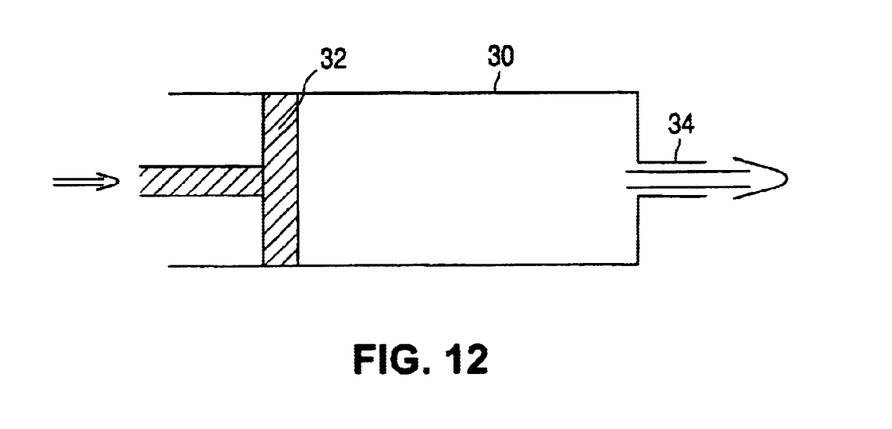
FIG. 12 is a side cross sectional view of a syringe pump.

Another example of a direct flow control pump is a conventional syringe pump, which has a cavity 30 of known dimensions, and a plunger 32 traveling through the cavity at a known velocity as illustrated in FIG. 12, whereby the fluid is pushed out of an outlet 34 of the cavity 30 at a known flow rate. One disadvantage of syringe pump is that they require a valve and time to reset the pump to the pumping position.

What different types of direct flow control pumps have in common is a cavity (e.g. flexible tube for displacement pumps, rigid cavity for syringe pumps) of known dimensions, and means for reducing the size of the cavity at a known rate (e.g. moving occlusion using a roller traveling at a know velocity for displacement pumps, moving plunger traveling at a known velocity through the cavity for syringe pumps), to force the fluid out of the cavity at known flow rates. Such pumps are largely unaffected by changes in fluid viscosity and back pressure, and are therefore ideal for operating the flow cell of the present invention.

The present invention has numerous advantages. A range of specimen fluid stream thicknesses can be selected based on the ratio of the cross section area of the passage 4 at the injection point I and the examination area 4c, as well as upon the specimen cannula shape. The exact specimen stream thickness at the examination area can also be finely adjusted by changing the sheath to specimen mass flow rate ratio (i.e. by changing the relative flow rates of the specimen fluid 10 and sheath fluid 12 supplied by pumps 14/16). A uniform flow is provided at a low pressure and a low mass flow rate. This enables high quality microscopic stopped flow (stroboscopic-illumination photography) analysis. The physical size of the flow cell is small because it employs a combination of geometric and linear flow rate focusing to obtain a thin focused specimen stream.

The performance of the flow cell is quite insensitive to the positioning of the cannula at the injection point I, because the specimen fluid exiting the cannula will rapidly adapt to that portion of the sheath fluid profile and velocity passing by the cannula. Thus, it is simply the cross sectional flow rate of the sheath fluid that must be controlled (given the location of the cannula), to produce the desired focusing. Any errors in positioning the cannula are compensated for by the affects of both linear flow rate and geometric focusing. Therefore, flow cell fabrication is simple and performance more robust. The specimen stream thickness at the examination area is not necessarily strongly dependent on the thickness of the cannula output end 2b because of linear flow rate and geometric focusing. The exact dimensions of the flow cell are not as critical either, as changes in flow rate focusing can correct for small errors in flow cell dimensions. This makes the manufacturing process less critical.

Figure 13:
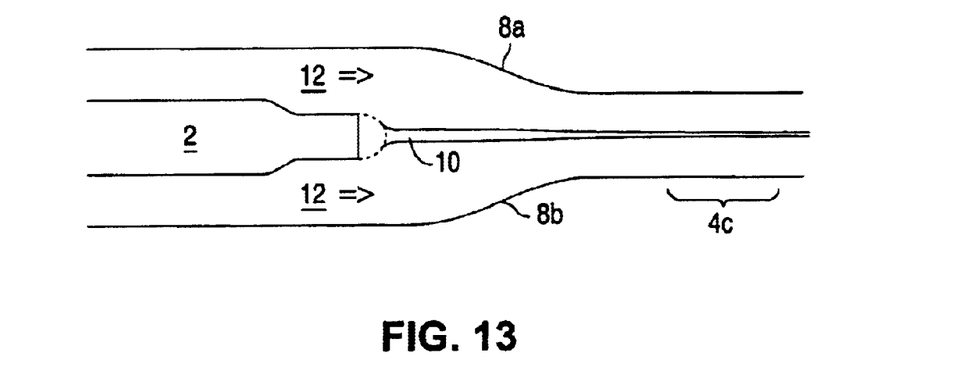
FIG. 13 is a side cross-section view of an alternate embodiment of the flow cell of the present invention, illustrating both top and bottom sloping walls for geometric focusing.

In the figures described above, the focusing portion 4b of passage 4 narrows because bottom wall 8b slopes toward top wall 8a (which is planar). Using a single sloping wall to narrow the passage focusing portion 4b can be easier to manufacture since only one shaped wall need be formed. However, top wall 8a can also, or alternatively, slope toward bottom wall 8b for contributing or causing outright the narrowing of the passage 4. FIG. 13 illustrates an alternate embodiment of the present invention, where both the top and bottom walls 8a/8b slope toward each other, with the injection fluid aligned to the center of the passage examination area 4c. In fact, side walls 8c and/or 8d could conceivably slope toward or away from each other to narrow or expand passage 4 in the orthogonal (width) cross section dimension, to assist in the geometric focusing of the specimen fluid in both cross section dimensions.

Exemplary Reduction to Practice

A flow cell according to the present invention has been reduced to practice, and is described below as a non-limiting example of the present invention. The output end 2b of the cannula 2 is shaped as an oblong ellipse. The long width W and short height H of the cannula output end 2b produces a stream of specimen fluid at the injection point I that is wider than the viewing area of the microscopic objective, and the specimen fluid thickness is determined by the degree of focusing desired. The passage 4 is preferably shaped to decrease in cross section area between the specimen injection point I and the specimen examination area 4c in one (cross section) dimension only to further focus (thin) the ribbon of specimen fluid oriented orthogonal to the examination area 4c. In this way, specimen fluid is presented in a flat stream with a direction of flow at right angles to the microscopic objective. However, focusing in the other (orthogonal) cross section dimension may be desired for some applications.

The flow cell housing is preferably constructed of a machined or molded material with parts cut out to form the passage focusing portion 4b and the flat examination area 4c. The housing material over examination area 4c is preferably made of a clear material (e.g. optical glass), so the images of the specimen fluid flowing underneath can be captured with minimal optical distortion.

The specimen fluid injected by the cannula into the passage 4 is about 150 microns thick (e.g. high) and 2 mm wide. At the injection point I, the passage 4 is about 6.2 mm high, and mainly contains sheath fluid. The variance of fluid velocities between the specimen fluid and the sheath fluid at the injection point I (for linear flow rate focusing) should not be too great to avoid excessive turbulence. The specimen fluid, surrounded by sheath fluid, proceeds to the examination area 4c of passage 4, which is about 4 mm wide and 150 microns high. The specimen fluid thickness at the point of injection I (~150 microns) is hydro-dynamically focused down via geometric and linear flow rate focusing to about 5 microns by the time it reaches examination area 4c.

The exemplary flow cell housing 6 was constructed of mostly plastic, except for optical glass over the examination area 4c. The upper portion of housing 6 (containing top wall 8a) was formed separately from lower portion of housing 6 (containing bottom wall 8b), which were sandwiched together using a sealing ring and adhesive to form the sealed passage 4. The use of lubricants that dissolve adhesive on the paper coating of the plastic is minimized. A plastic with an adhesive free protective coating was used. The faces of the plastic parts that join to the optical glass were smooth and even, and not machined. All faces that were machined were polished to insure that they are flat and smooth.

The exemplary flow cell was fabricated in a dust free environment (e.g. clean room, a clean box with a HEPA filter, powder free latex gloves, etc.). The optical faces of the optical glass were never touched. Protective adhesive coatings on the optical faces were not removed until absolutely necessary, to reduce the possibility of contaminating the optical faces with debris. Any dust was removed with particle free compressed air. All parts were covered with lint free lens paper after fabrication was complete or when an operation was interrupted, and stored in a dust free container. Surface dimensions where checked to not vary by more than about 0.001 inches from side to side and along widths. Parts were sonicated for five minutes in 99% isopropyl alcohol, and blown dry with particle free air. A lint free cloth wetted with isopropyl alcohol was also used to clean parts.

The fabrication of the cannula 2 is next described. This fabrication technique, and the actual shaped cannula formed thereby, is exemplary only, and should not be deemed as limiting a cannula suitable for use as part of the present invention.

The cannula 2 was made from extra-thin wall, 16 gauge stainless steel tubing. Two mandrels were used to shape the cannula output end 2b. The first mandrel was formed by cutting a piece of 0.010 inch thick stainless steel shim stock in a triangle shape having a width of about 0.080 inches and a length of about 0.50 inches. The second mandrel was formed by cutting a piece of 0.006 inch thick stainless steel shim stock in a triangle shape having a width of about 0.125 inches and a length of about 0.50 inches.

The stainless steel tubing was cut to a desired length (e.g. 2.5 inches). While turning the tube in a lathe, one end (hereinafter referred to the prepared end, which will form the output end 2b of the cannula 2) of the tube was squared using a fine pitch file. The edge of the cut was blended to about ¼ to ⅓ of the wall thickness. A 600 grit (wet-or-dry) sandpaper was used to polish the prepared end (about 0.25 inches) of the tube. The tube was then removed from the lathe and the inside of the prepared end was manually deburred with a sharp blade. A torch was used to heat the prepared end of the tube to an orange color (about ¼ to ⅜ inch), which was then allowed to cool slowly. The softened steel turned a dull blue-gray color (where a shiny surface may be restored by lightly sanding the gray area with 600 grit wet-or-dry sandpaper).

The 0.010 inch mandrel was pushed into the prepared end of the tube. About 0.150 inch of the prepared end of the tube was placed into the jaws of a precision machinists vise, with the mandrel parallel to the jaws of the vise. The vise was slowly tightened to crush the tube onto the 0.010 inch mandrel. The tube was removed from the vice, and the 0.010 inch mandrel was removed from the tube. The 0.006 inch mandrel was then inserted firmly into the prepared end of the tube. The tube was placed into the jaws of the vise in the same position as before, and crushed onto the 0.006 inch mandrel. The 0.006 inch mandrel was removed from the tube end. Using two different mandrels of different thicknesses in two different crushing steps helps prevent crumpling of the tube's edges.

The tube was then cut to its desired overall length (e.g. 0.870 inches (+0.020/−0.000)). The newly cut end was dressed with 600 grit wet-or-dry sandpaper, and deburred with a sharp blade, so that the edges were smooth and no material extended beyond the diameter of the tube body. The finished cannula was then washed in an ultrasonic cleaner with deionized water. Residue was removed with compressed air injected into the flattened (prepared) end of the cannula. The 0.006 inch mandrel fit into the prepared end of the tube with only light resistance.

It is to be understood that the present invention is not limited to the embodiment(s) described above and illustrated herein, but encompasses any and all variations falling within the scope of the appended claims. For example, materials, processes and numerical examples described above are exemplary only, and should not be deemed to limit the claims. The microscope/camera can form part of the housing that contains the fluids in the passage 4. For the purposes of this disclosure, height and width simply refer to orthogonal cross section dimensions, and are interchangeable depending upon the orientation of the view of the flow cell. Likewise, top and bottom walls, and left and right walls, are interchangeable by flipping the orientation of the view of the flow cell (i.e. flipping the flow cell over). While the flow cell is illustrated with an imager for capturing images of the specimen fluid stream passing through the examination area, the imager could in fact be any optical measurement device (e.g. photo sensors, etc.) that measures any optical parameter (optical transparency, optical scattering, fluorescence, etc.) of the fluid stream. Alternately (and/or additionally), the imager could instead be (or additionally be) a measuring device that measures one or more non-optical parameters as well (e.g. electrical parameters such as resistance or capacitance, ultrasonic parameters, etc.). Lastly, it is possible to override the geometric focusing of the flow cell by injecting the specimen with a velocity that is higher than that of the sheath fluid. In such a case, the specimen cross section at the examination area would be thicker than that obtained by geometric focusing alone, which may be desirable to compensate for excessive geometric focusing for some applications. This allows for compensation for some sample/sheath fluid viscosity combinations that would otherwise require a different dimensioned flow cell.

What is claimed is:

1. A flow cell for examining specimen fluid flowing with sheath fluid, comprising:
    a housing defining a hollow fluid passage that includes an injection point, a geometric focusing portion in which the fluid passage narrows in a cross section dimension thereof, and an examination area;
    a cannula having an output end disposed at the injection point in the fluid passage;
    a first direct flow control pump for pumping the sheath fluid through the fluid passage such that the sheath fluid has a first known velocity at the injection point;
    a second direct flow control pump for pumping the specimen fluid through the cannula such that the specimen fluid is injected into the fluid passage by the cannula output end as a stream of the specimen fluid having a second known velocity at the injection point, wherein the second known velocity is different from the first known velocity; and
    a measurement device for measuring a parameter of the specimen fluid stream passing through the examination area;
    wherein a cross section dimension of the specimen fluid stream is focused by the sheath fluid via linear flow rate focusing and by the narrowing geometric focusing portion of the fluid passage via geometric focusing.

2. The flow cell of claim 1, wherein:
    the second known velocity is lean than the first known velocity; and
    the cross section dimension of the specimen fluid stream is focused down by the sheath fluid via linear flow rate focusing.

3. The flow cell of claim 1, wherein:
    the hollow fluid passage includes a top wall and a bottom wall that define the cross section dimension of the fluid passage therebetween; and
    a portion of the bottom wall slopes toward the top wall to cause the narrowing of the cross section dimension of the geometric focusing portion of the fluid passage.

4. The flow cell of claim 1, wherein:
the hollow fluid passage includes a top wall and a bottom wall that define the cross section dimension of the fluid passage therebetween; and
portions of the top and bottom walls slope toward each other to cause the narrowing of the cross section dimension of the geometric focusing portion of the fluid passage.

5. The flow cell of claim 1, wherein the cross section dimension of the fluid passage at the examination area is less than the cross section dimension of the fluid passage at the injection point.

6. The flow cell of claim 1, wherein at the injection point, the cross section dimension of the specimen fluid stream is less than an orthogonal cross section dimension of the specimen fluid stream.

7. The flow cell of claim 1, wherein the housing includes a port extending from the fluid passage, and wherein the flow cell further includes:
a third pump for pumping air bubbles from the fluid passage via the port.

8. The flow cell of claim 1, wherein:
the cannula includes an input end for receiving the specimen fluid;
the cannula input end has a first cross-section area; and
the cannula output end has a second cross-section area that is smaller than the first cross-section area.

9. The flow cell of claim 8, wherein:
the first cross-section area is substantially round in shape; and
the second cross-section area is substantially elliptical in shape.

10. The flow cell of claim 1, wherein the measurement device measures an optical parameter of the specimen fluid stream.

11. The flow cell of claim 1, wherein the optical measurement device includes an imager for capturing images of the specimen fluid stream passing through the examination area.

12. The flow cell of claim 11, wherein:
the housing includes a transparent portion adjacent the examination area; and
the imager includes a microscope and camera for capturing the images of the specimen fluid through the transparent portion of the housing.

13. The flow cell of claim 1, wherein:
the first direct flow control pump includes:
a compression tube for containing the sheath fluid;
a compression surface; and
a roller for incrementally compressing the compression tube against the compression surface to create a moving occlusion of the compression tube that pushes the sheath fluid through the compression tube at a known velocity, the second direct flow control pump includes;
a compression tube for containing the specimen fluid;
a compression surface; and
a roller for incrementally compressing the compression tube against the compression surface to create a moving occlusion of the compression tube that pushes the specimen fluid through the compression tube at a known velocity.

14. A method of flowing specimen fluid and sheath fluid through a hollow fluid passage of a flow cell having an injection point, a geometric focusing portion in which the fluid passage narrows in a cross section dimension thereof, and an examination area, the method comprising;

flowing the sheath fluid through the fluid passage such that the sheath fluid has a first known velocity at the injection point;
injecting the specimen fluid into the fluid passage at the injection point as a stream of the specimen fluid having a second known velocity, wherein the second known velocity is different from the first known velocity; and
measuring a parameter of the specimen fluid stream passing through the examination area;
wherein a cross section dimension of the specimen fluid stream is focused by the sheath fluid via linear flow rate focusing and by the narrowing geometric focusing portion of the fluid passage via geometric focusing.

15. The method of claim 14, wherein the injection of the specimen fluid is performed using a cannula having an input end for receiving the specimen fluid and an output end disposed at the injection point in the fluid passage for injecting the specimen fluid.

16. The method of claim 15, wherein:
the cannula input end has a first cross-section area; and
the cannula output end has a second cross-section area that is smaller than the first cross-section area.

17. The method of claim 16, wherein:
the first cross-section area is substantially round in shape; and
the second cross-section area is substantially elliptical in shape.

18. The method of claim 14, wherein:
the second velocity is less than the first velocity; and
the cross section dimension of the specimen fluid stream is focused down by the sheath fluid via liner flow rate focusing.

19. The method of claim 14, wherein:
the hollow fluid passage includes a top wall and a bottom wall that define the cross section dimension of the fluid passage therebetween; and
a portion of the bottom wall slopes toward the top wall to cause the narrowing of the cross section dimension of the geometric focusing portion of the fluid passage.

20. The method of claim 14, wherein:
the hollow fluid passage includes a top wall and a bottom wall that define the cross section dimension of the fluid passage therebetween; and
portions of the top and bottom walls slope toward each other to cause the narrowing of the cross section dimension of the geometric focusing portion of the fluid passage.

21. The method of claim 14, wherein the cross section dimension of the fluid passage at the examination area is less than the cross section dimension of the fluid passage at the injection point.

22. The method of claim 14, wherein at the injection point, the cross section dimension of the specimen fluid stream is less than an orthogonal cross section dimension of the specimen fluid stream.

23. The method of claim 14, further comprising:
withdrawing air bubble from the fluid passage.

24. The method of claim 14, wherein the measurement of the parameter includes measuring an optical parameter of the specimen fluid stream.

25. The method of claim 14, wherein the measurement of the parameter includes capturing images of the specimen fluid stream passing through the examination area.

* * * * *